(12) United States Patent
Neto

(10) Patent No.: US 10,253,334 B2
(45) Date of Patent: Apr. 9, 2019

(54) THERAPEUTIC SERUM OBTAINED FROM CO-CULTURED CELLS

(71) Applicant: Serucell Corporation, Palo Alto, CA (US)

(72) Inventor: Walter De Paula Neto, Lavalette, WV (US)

(73) Assignee: SERUCELL CORPORATION, Palo Alto, CA (US)

(*) Notice: Subject to any disclaimer, the term of this patent is extended or adjusted under 35 U.S.C. 154(b) by 0 days.

(21) Appl. No.: 16/047,410

(22) Filed: Jul. 27, 2018

(65) Prior Publication Data

US 2018/0340190 A1    Nov. 29, 2018

Related U.S. Application Data

(63) Continuation of application No. 15/943,320, filed on Apr. 2, 2018, which is a continuation-in-part of application No. 15/700,895, filed on Sep. 11, 2017, now Pat. No. 9,974,813, which is a continuation-in-part of application No. 14/597,796, filed on Jan. 15, 2015, now Pat. No. 9,907,745.

(60) Provisional application No. 61/927,674, filed on Jan. 15, 2014.

(51) Int. Cl.

| | |
|---|---|
| C12P 21/00 | (2006.01) |
| C12P 1/00 | (2006.01) |
| A61K 8/67 | (2006.01) |
| A61K 8/98 | (2006.01) |
| A61K 45/06 | (2006.01) |
| A61Q 19/00 | (2006.01) |
| A61K 9/00 | (2006.01) |
| A61K 35/12 | (2015.01) |
| C12N 5/00 | (2006.01) |
| A61K 9/14 | (2006.01) |
| C12N 5/077 | (2010.01) |
| A61Q 19/08 | (2006.01) |

(52) U.S. Cl.
CPC .............. *C12P 1/00* (2013.01); *A61K 8/671* (2013.01); *A61K 8/676* (2013.01); *A61K 8/981* (2013.01); *A61K 9/0014* (2013.01); *A61K 9/145* (2013.01); *A61K 35/12* (2013.01); *A61K 45/06* (2013.01); *A61Q 19/00* (2013.01); *A61Q 19/08* (2013.01); *C12N 5/0018* (2013.01); *C12N 5/0081* (2013.01); *C12N 5/0652* (2013.01); *A61K 2800/10* (2013.01); *A61K 2800/70* (2013.01); *C12N 2500/30* (2013.01)

(58) Field of Classification Search
CPC ..................................................... C12P 21/00
See application file for complete search history.

(56) References Cited

U.S. PATENT DOCUMENTS

| | | | |
|---|---|---|---|
| 4,016,036 A | 4/1977 | Green et al. | |
| 5,561,107 A | 10/1996 | Jaynes et al. | |
| 6,191,110 B1 | 2/2001 | Jaynes et al. | |
| 7,118,746 B1 | 10/2006 | Naughton et al. | |
| 8,138,147 B2 | 3/2012 | Naughton et al. | |
| 8,246,969 B2 | 8/2012 | Engles et al. | |
| 8,246,971 B2 | 8/2012 | Engles et al. | |
| 8,257,947 B2 | 9/2012 | Naughton et al. | |
| 8,268,336 B2 | 9/2012 | Engles et al. | |
| 8,361,485 B2 | 1/2013 | Naughton et al. | |
| 8,476,231 B2 | 7/2013 | Naughton et al. | |
| 8,518,422 B2 | 8/2013 | Monks et al. | |
| 8,524,494 B2 | 9/2013 | Naughton et al. | |
| 8,530,415 B2 | 9/2013 | Naughton et al. | |
| 8,535,913 B2 | 9/2013 | Naughton et al. | |
| 9,034,312 B2 | 5/2015 | Naughton et al. | |
| 2001/0048917 A1 | 12/2001 | Hoeffler et al. | |
| 2004/0116356 A1 | 6/2004 | Malik | |
| 2006/0115460 A1 | 6/2006 | Naughton | |
| 2006/0165667 A1 | 7/2006 | Laughlin et al. | |
| 2007/0237750 A1 | 10/2007 | Naughton | |
| 2009/0202654 A1 | 8/2009 | Nixon | |
| 2010/0166824 A1 | 7/2010 | Naughton et al. | |
| 2011/0177015 A1 | 7/2011 | Friedlander | |

(Continued)

FOREIGN PATENT DOCUMENTS

| | | |
|---|---|---|
| CA | 2367281 | 9/1999 |
| CA | 2983832 | 11/2016 |
| EP | 1375646 | 1/2004 |

(Continued)

OTHER PUBLICATIONS

Berse et al. (1999) Clin. Exp. Immunol. 115: 176-182, cited in U.S. Appl. No. 14/597,796.
Garner(1998) Plastic and Reconstructive Surgery, vol. 102, No. 1, 135-139, cited in U.S. Appl. No. 14/597,796.
Ghaffari et al. (2009) J. Invest. Dermatol. vol. 129, 340-347, cited in U.S. Appl. No. 14/597,796.
Hawley-Nelson (1980) J. Invest. Dermatol. 75: 176-182, cited in U.S. Appl. No. 14/597,796.

(Continued)

*Primary Examiner* — Rosanne Kosson
(74) *Attorney, Agent, or Firm* — Andrew D. Wright; Roberts Mlotkowski Safran Cole & Calderon, P.C.

(57) ABSTRACT

A therapeutic serum suitable for inclusion in a cosmetic preparation may be produced by stressing a co-culture including proliferative cells. The co-culture of cells may be obtained by growing first culture to less than one-hundred percent confluence on a surface. After a monolayer of first culture is established, a second culture may be seeded onto at least one cell free area on the surface, the resulting co-culture grown to less than one-hundred percent confluence. Additional cultures may then be seeded onto cell free areas of the surface and established until a monolayer having the desired population of cells is obtained. The monolayer is then stressed to obtain a serum by conditioning a collection medium. The obtained serum may be combined with a suitable cosmetic base to provide a cosmetic preparation.

16 Claims, No Drawings

(56) References Cited

U.S. PATENT DOCUMENTS

2015/0196484 A1 7/2015 Neto
2018/0117092 A1 5/2018 Naughton et al.

FOREIGN PATENT DOCUMENTS

| WO | 2006014089 | 2/2006 |
| WO | 2007005659 | 1/2007 |
| WO | 2010086754 | 8/2010 |
| WO | 2011006107 | 1/2011 |
| WO | 2011138687 | 11/2011 |

OTHER PUBLICATIONS

Kubo et al. (1984) J. Invest. Dermatol. 82: 580-586, cited in U.S. Appl. No. 14/597,796.
Li et al. (1010) FEBS J. 277: 3688-3698, cited in U.S. Appl. No. 14/597,796.
Lim et al. (2002) Am. J. Physiol. Cell Physiol. 283: C212-C222, cited in U.S. Appl. No. 14/597,796.
Wong et al. (2007) British Journal of Dermatology 156: 1149-1155, cited in U.S. Appl. No. 14/597,796.

THERAPEUTIC SERUM OBTAINED FROM CO-CULTURED CELLS

CROSS-REFERENCE TO RELATED APPLICATIONS

This Application is a continuation of U.S. application Ser. No. 15/943,320, filed Apr. 2, 2018, the teachings of which are hereby incorporated by reference in their entirety, which is a continuation-in-part of U.S. application Ser. No. 15/700,895, filed Sep. 11, 2017, the teachings of which are hereby incorporated by reference in their entirety, which is a continuation-in-part of U.S. application Ser. No. 14/597,796, filed Jan. 15, 2015, the teachings of which are hereby incorporated by reference in their entirety, which claims priority to Provisional U.S. Application No. 61/927,674, filed Jan. 15 2014, the teachings of which are hereby incorporated by reference in their entirety.

FIELD

A therapeutic serum, a method of obtaining such serum, and medical devices and preparations containing such serum are provided.

BACKGROUND

The various organs of the body are composed of multiple cell types working together. By working together, the different cell types maintain the health the organ and help the organ recover from injury. Consider, for instance, the largest organ of the body, skin.

Skin is an essential multilayer organ. Providing a barrier against pathogens and toxins, as well as synthesizing nutrients such as vitamin D, skin is essential for maintaining an individual's physical health. The integrity of skin is also essential for maintaining one's psychological health. Skin is the most prominent part of an individual's body. Blemishes, scars, wrinkles and perceived imperfections can diminish an individual's self-confidence. Maintaining physical and psychological health, therefore, requires maintaining healthy skin.

Healthy skin comprises layers of different cells supported by a scaffolding of proteins called the extracellular matrix. The extracellular matrix supporting the skin comprises various proteins such as collagen, fibronectin and laminin. These and other structural proteins intertwine and communicate to form the structural and dynamic three-dimensional scaffolding providing skin with its strength and resilience. Cells forming the various layers of skin adhere to the extracellular matrix, and rely on both structural and biologically active signal relaying molecules within the matrix to maintain proper function. During wound healing, cells also use the extracellular matrix as a bridge to migrate into and close wounds. Providing support and pathways for healing, the extracellular matrix is an important structural and biologically active component of healthy skin. As an individual ages, however, the extracellular matrix changes and becomes weakened, leading to the appearance of wrinkles, blemishes and decreased healing.

The extracellular matrix is manufactured and maintained primarily by fibroblasts beneath the skin's surface. Manufacturing and maintaining the biological activity of the extracellular matrix, healthy fibroblasts are essential for healthy skin. Above the fibroblasts, on top of the extracellular matrix, are keratinocytes forming the epidermis. Forming the epidermis, the outer layer of skin, healthy keratinocytes are also essential for the appearance and integrity of skin. Signaling between keratinocytes and immune cells helps to maintain homeostasis of the skin and protect against infections. Accordingly, maintaining healthy skin from its base to its surface requires promoting the health of different cells throughout the layers of skins.

The same is true for other organs of the body. The nervous system, for instance, is composed of various neurons and glial cells. Carrying signals to and from the brain, as well as processing information within the spinal cord and brain, neurons are often thought of as the primary workhorses of the nervous system. Neurons, however, are supported by various glial cells. For instance, astrocytes maintain the health of neurons and help the brain recovery from various injuries, such as stroke. Schwan cells insulate peripheral nerves and help them regenerate after injury. Accordingly, just like the skin, the health and healing of the nervous system requires the promoting the health of different cells.

The liver, another important organ of the body, also relies on multiple cell types to maintain health and healing. Repairing and maintaining the extracellular matrix, stellate cells, for instance, are important for maintaining health and healing.

SUMMARY

A serum collected from a growing co-culture of cells may provide the various proteins, cytokines, glycans, hormones and other molecular factors necessary for promoting the health of and healing various organs of the body. Given the importance of the extracellular matrix in organs, such may be accomplished by remolding and maintenance of the extracellular matrix, as to promote wound healing, promote homeostasis, help maintain the integrity of the organ and/or scars. Given that organs are composed of different cell types acting in concert, collecting a serum from a co-culture comprising various cells types would better match the complete needs of injured and/or aging organs. Healthy skin, for instance, comprises various cells, such as keratinocytes, fibroblasts, mesodermal cells, melanocytes, Merkel Cells, Langerhans cells, etc., collecting a serum from a growing co-culture comprising keratinocytes, fibroblasts, mesodermal cells, melanocytes, Merkel Cells, Langerhans cells, T-cells and/or other skin cells in various combinations would better match the complete needs of new and aging skin. Similarly, collecting a serum from a co-culture of hepatocytes, stellates, Kupffer cells and/or endothelial cells would better match the needs of injured, diseased and/or aging livers. Collecting a serum from a co-culture of comprising all or a portion of the various cells within nervous system, likewise, may assist the nervous system in recovering from injury and age. However, different growth rates and/or nutrients requirements may complicate efforts to co-culture different cells. A portion of the cells to be co-cultured, for instance, may only be able to survive in a growth medium that promotes the proliferation of other cells within the co-culture. With some cells proliferating and others only surviving, the cultures could be become dominated by the proliferating cells. That is, the resulting co-culture may comprise disproportionate amounts of the various cell types. Dominated by one type of cell over the other types, intercellular signaling, such as paracrine signaling, may be altered, diminished and/or lost. Having altered and/or diminished intercellular signaling, such a culture would be unlikely to produce a serum having all the proteins and/or other molecular factors necessary for healing and promoting the health of injured and/or aging organs.

Dominance by one cell type, i.e. a disproportionate amount, within a co-culture may be avoided by seeding a first surface with a first culture of cells and allowing the culture to become established by growing the first culture to a monolayer of less than one-hundred percent confluence. Growing the first culture to a monolayer of less than one-hundred percent confluence may be facilitated by growing the first culture in the presence of a growth medium comprising nutrients and at least one growth factor. The first growth medium should promote the proliferation of the first cell culture. Growing the first culture to less than one-hundred percent confluence provides at least one cell free area on the first surface. A second culture of cells may then be seeded onto at least a portion of the cell free areas of the first surface. The second culture of cells may comprise cells different than the first culture. After being seeded onto at least one of the cell free surface areas of the first surface, the second culture and first culture can be grown to less than one-hundred percent confluence in the presence of a second growth medium. The second growth medium should promote the proliferation of the second culture and may comprise nutrients and at least one growth factor. Depending upon the cells within the first and second cultures, the first growth medium and second growth medium may be identical, include shared components and/or be completely different. Accordingly, the second growth medium may comprise the nutrients and at least one growth factor of the first growth medium. The procedure may be repeated with subsequent cell cultures and subsequent growth medium, which may allow for complex and/or diverse co-cultures. Following the general procedure of seeding subsequent cultures onto cell free areas of a surface may facilitate establishment of a co-culture by providing the subsequent cultures room and/or favorable conditions to become established. Favorable conditions may be provided by changing the growth medium and/or other conditions, such as temperature and/or pH, as to promote proliferation of the subsequently seeded cultures. Favorable conditions promoting the proliferation of subsequently seeded cultures should not be such as to cause previously seeded cultures to become senescent. The serum collected from a co-culture of cells may be enhanced by maintaining the cells in a proliferative phase by growing the final co-culture to less than 100% confluence on the first surface after seeding the final culture to be added. Maintaining the cells in a proliferative phase prior to and/or during serum collection may influence the composition of the serum.

Production of the serum may be induced in a co-culture by replacing the first and/or second growth medium with a collection medium lacking all or a portion of the growth factors of the final growth medium, after the final co-culture has been grown to less than one-hundred percent confluence. For instance, the final growth medium may be replaced with a collection medium lacking at least one of the growth factors of the second growth medium. The collection medium may comprise the nutrients of at least one of the first and second growth mediums. The co-culture may then be maintained for a period of time in the collection medium sufficient to allow the co-culture to produce from the collection medium a conditioned medium comprising the therapeutic serum. After which, at least a portion of the conditioned medium containing the therapeutic serum may be collected.

Facilitating growth of a monolayer may be accomplished by utilizing a surface enabling growth of the co-culture radially outwards as a single layer from each seed cell and/or collection of cells. Seeding a surface comprises depositing cells of the culture to be grown onto the surface. Depending on the manner utilized to deposit cells onto the surface, the cells may be deposited as individuals or clusters. For instance, seeding the cells from a solution may cause individual cells to be deposited over the area of the surface seeded. In combination or the alternative, the surface may be seeded by depositing tissue samples and/or portions of a previously grown culture onto the surface. In such instances, clusters of cells may be deposited onto the area of the surface seeded. The surface should allow the culture to grow radially outwards from deposited cells. Of course, portions of the culture growing radially outward from individually seeded cells and/or clusters may merge together. The cells may also coalesce together to form various three-dimensional configurations. Hepatocytes, for instance, may self-assemble into spheroids. Accordingly, a monolayer may comprise various three-dimensional aggregates, provided that such aggregates and other cells within the co-culture are predominately arranged as a single layer.

Radial growth from seeded cells and/or clusters providing a monolayer may be facilitated with a variety of surfaces. For instance, the bottom of Erlenmeyer flask and/or petri dish may provide a sufficient surface. The sides of T-flask may also provide a sufficient surface. When vessels such as a petri dishes and/or flasks are utilized, they should be sized to provide a sufficient volume of growth medium enabling growth of the final co-culture to be obtained.

The surface does not need to be the sides of a vessel. For instance, the surface may be one or more plates submerged in a growth medium.

The surface may also be provided by a gelling agent, such as agar. In such instances, the culture could be grown on the solidified gelling agent. The gelling agent may include all or a portion of the growth medium. When the gelling agent does not include all of the growth medium, the missing elements of the growth medium may be provided by submerging the solidified gelling agent in an appropriate solution.

As to facilitate growth and establishment, a first and/or subsequent culture may be provided with a growth medium comprising nutrients and growth factors. Growth factors are substances capable of stimulating healing, growth, cellular proliferation and/or cellular differentiation. Growth factors useful for facilitating growth and establishment of a culture of skin cells may include, but are not limited to, amino acids, such as L-Glutamine, hormones, such as hydrocortisone hemisuccinate, insulin and/or epinephrine, omega fatty acids, such as linoleic acid, vitamins, such as vitamin C, proteins, such as serum albumin, basic fibroblasts growth factor, acidic fibroblasts epidermal growth factor, transforming growth factor, insulin, bovine pituitary extract and/or ApoTransferin, and/or glycerophospholipids, such as lecithin. Other growth factors may facilitate the growth of the other cells to be co-cultured. Accordingly, the growth factors added may be chosen to promote the growth and/or proliferation of a culture.

The nutrients in the growth medium provided to a culture need not be lavish or exceed the minimal nutrients required for survival and growth of the culture. As such, a basal medium and/or minimal essential medium can provide sufficient nutrients. The nutrients of the first, second and/or other subsequent growth medium, therefore, may be provided by a basal medium. Accordingly, the first, second and/or other subsequent growth medium provided to a culture may comprise growth factors combined with a basal medium and/or minimal essential medium. The growth medium provided to a first, second and/or other subsequent cultures may include a balancing agent to buffer the medium to a desired pH, such as, but not limited to, Earl's salts and/or 4-(2-hydroxyethyl)-1-piperazineethanesulfonic acid (HEPES).

Accordingly, when establishing a co-culture of cells, a first seeded culture may be provided with a growth medium comprising nutrients and at least one growth factors as to facilitate establishment of the culture after being seeded onto a surface. The growth medium provided to the first seeded culture may comprise a basal medium and/or minimal essential medium. The growth factors included within the growth medium provided to the first and/or subsequent seeded cultures may include, but are not limited to, amino acids, such as L-Glutamine, hormones, such as hydrocortisone hemisuccinate, insulin and/or epinephrine, omega fatty acids, such as linoleic acid, vitamins, such as vitamin C, proteins, such as serum albumin, basic fibroblasts growth factor, epidermal growth factor, transforming growth factor, insulin, bovine pituitary extract and/or ApoTransferin, and/or glycerophospholipids, such as lecithin.

Different growth rates and/or nutrients requirements may complicate efforts to co-culture different cells. Keratinocytes, for instance, may only be able to survive in a growth medium that promotes the proliferation of T cells. Consequently, attempting to co-culture T-cells with keratinocytes and/or other skin cells can easily result in a culture in which not all cell types are proliferating. With some cell types proliferating and others only surviving, the cultures could be become dominated by the proliferating cells. Being dominated by one type of cell over the other types, intercellular signaling, such as paracrine signaling, may be altered, diminished and/or lost. Having altered and/or diminished intercellular signaling, such a culture would be unlikely to produce a serum having all the proteins and/or other molecular factors necessary for healing and promoting the health of wounded and/or aging skin.

For instance, traditional keratinocyte mediums, such as Dulbecco's Modified Eagle Media (DMEM), Keratinocyte Growth Medium (KGM, Lonza) and Roswell Park Memorial Institute medium (RMI medium), are effective for promoting the proliferation of keratinocytes. However, such mediums may not sufficiently promote the growth and survival and T-cells. The resulting co-culture, accordingly, may be dominated by keratinocytes. Attempting to co-culture keratinocytes and T-cells in a growth medium promoting the survival and growth of T-cells, such as Xvivo15 from Lonza, may not promote the proliferation of keratinocytes. Utilizing a medium not promoting the proliferation of keratinocytes, the resulting culture may be dominated by T-cells. Dominated by keratinocytes or T-cells, the natural paracrine signaling between the cells may be lost. Paracrine signaling between keratinocytes and T-cells may stimulate the production of molecular factors, such as cytokines like IL-17, useful for promoting homeostasis of the skin and defending against fungal and bacterial infections. A serum comprising such homeostasis and/or defensive molecular factors may be beneficial in promoting the health of skin and/or other organs. In combination or the alternative, a serum comprising such homeostasis and/or defensive molecular factors may be beneficial in protecting organs from infection. Co-cultures dominated by keratinocytes or T-cells may not provide such beneficial serums due to intercellular signaling, such as paracrine signaling, being altered, diminished and/or lost.

Dominance by one cell type within a co-culture may be avoided by seeding a surface with a first culture and growing the first culture to a monolayer of less than one-hundred percent confluence in the presence of a first growth medium comprising nutrients and at least one growth factor, as to provide at least one cell free area. All or a portion of the cell free areas of the first surface may then be seeded with a second culture. After seeding of the second culture, the first and second cultures may be grown to a monolayer of less than one-hundred percent confluence in the presence of a second growth medium comprising nutrients and at least one growth factor. The second growth medium should promote proliferation of the second culture. Accordingly, in the case of a co-culture of T-cells and keratinocytes, the first culture may comprise keratinocytes and the first growth medium may comprise a growth medium promoting the proliferation of the keratinocytes, such as DMEM, KGM or RMI medium. After the keratinocytes have been grown to a sufficient monolayer, the first surface may be washed to remove the first growth medium. All or a portion of the cell free areas on the first surface may then be seeded with a second culture comprising T-cells. The second and first culture may then be grown to a monolayer of less than one-hundred percent confluence in the presence of a second growth medium promoting the proliferation of T-cells, such as Xvivo15. As to maintain at least some level of proliferation of the first culture, the second medium may comprise at least one growth factor facilitating and/or promoting the proliferation of the first culture and/or intervening cultures. For instance, if the first culture comprises keratinocytes, the second growth medium may comprise at least one of bovine pituitary extract, L-glutamine, hydrocortisone hemisuccinate, transforming growth factor, insulin, epinephrine, and ApoTransferrin, or combinations thereof.

Different responses to growth factors may also complicate efforts to co-culture different types of cells. For instance, hepatocytes can spontaneously form spheroids when cultured. The formation of spheroids, however, is inhibited by fetal bovine serum. Obtaining a monolayer comprising hepatocytes spheroids, accordingly, requires limiting and/or precluding exposure to fetal bovine serum. Stellates, another cell of the liver, require the presence of FBS to grow in culture. Providing a second culture comprising hepatocyte spheroids after a first culture of stellates may require replacing a first growth medium comprising FBS with a second growth medium lacking FBS. The second growth medium, therefore, may lack a nutrient and growth factor of the first growth medium.

Attempts to co-culture different types of cells may also be complicated by different growth rates in response to the growth medium. A growth medium including basic fibroblast growth factor (bFGF) stimulates proliferation of fibroblasts more than keratinocytes. Conversely, acidic FGF stimulates proliferation of keratinocytes more than fibroblasts. As such, an acidic growth medium may cause a co-culture of fibroblast and keratinocytes to be dominated by keratinocytes, whereas a basic growth medium may cause the co-culture to be dominated by fibroblast. Being dominated by fibroblast over keratinocytes, or vice versa, intercellular signaling, such as paracrine signaling, may be altered, diminished and/or lost. Having altered and/or diminished intercellular signaling, such a culture would be unlikely to produce a serum having all the proteins and/or other molecular factors necessary for healing and/or promoting the health of injured and/or aging organs.

Dominance by one cell type over another due to different responses to growth factors may be lessened and/or avoided by removing growth factors favoring proliferation of previous seeded cultures prior to growing later seeded cultures. In combination or the alternative, the growth factors favoring the later seeded culture may be added to the growth medium. Accordingly, the first growth medium may comprise a growth factor promoting the proliferation of a first seeded culture. In some instances, the first growth medium may comprise growth factors promoting the proliferation of the first culture more than subsequent cultures. For instance, if the first culture comprises fibroblast cells, the first growth medium may comprise bFGF. After the first seeded culture has been grown to a monolayer of less than one-hundred percent confluence, as to provide at least one cell free area, the first surface may be washed to remove the first growth medium. A second cell culture may then be seeded onto all or a portion of the cell free area. The first and second cultures may then be grown to a monolayer of less than one-hundred percent confluence in the presence of a second growth medium. The second growth medium may comprise a growth factor promoting the proliferation of cells within the second culture more than cells within the first culture. For instance, if the second culture comprise keratinocytes, the second growth medium may comprise aFGF. As to maintain at least some level of proliferation of the first culture, the second medium may comprise at least one growth factor facilitating and/or promoting the proliferation of the first culture and/or intervening cultures.

Attempts to co-culture different types of cells may also be complicated by different growth rates of the cells, regardless of the growth medium. Some cells of the intended co-culture may be slow to proliferate with respect to other cells of the co-culture across many different growth mediums. Growing quicker than other cells within the co-culture, the faster proliferating cells may crowd out the other cells within the co-culture. Consequently, attempting to co-culture faster proliferating cells with slower proliferating cells may result in a co-culture dominated by the faster proliferating cells over the slower proliferating cells.

Dominance by one cell type over another due to different growth rates may be lessened and/or avoided by allowing slower growing cells to create a sufficient monolayer on a surface prior to seeding faster growing cells onto the surface. For instance, the first seeded culture may comprise cells with slower doubling times than other cells to be cultured. After the first seeded culture has been sufficiently established on the surface, cultures comprising more proliferative cells can be seeded onto at least one cell free area on the surface to provide a co-culture. Once the more proliferative cells have been established, subsequent cultures can be seeded and established until a co-culture having the desired cellular composition is obtained on the surface. Achieving the desired cellular composition of the final co-culture may require seeding successive cultures onto the surface at varying confluences. For example, if the final co-culture is to comprise a co-culture of a first cell type, a second cell type with faster growth rate than the first cell type, and a third cell type with a faster growth rate than the first and second cell types, then it may be appropriate to first seed a culture of the slowest growing cells onto the surface and grow the first seeded culture to approximately thirty-three percent confluence. A culture of cells having the intermediate growth rate may then be seeded onto at least one cell free area on the first surface. The co-culture of the first and second cell types may then be grown to approximately sixty-six percent confluence. Then a culture of the fastest growing cell types may be seeded onto at least one cell free area on the first surface and the co-culture of the three cells grown to less than one-hundred percent confluence.

The above examples are based upon situations in which subsequent seeded cultures comprise cells growing sufficiently faster than previously seeded cultures such that the growth of previously seeded cultures can be treated as halted, and that a final co-culture having equal amounts of each culture is desired. One or both these assumptions may not be true for every co-culture to be produced. Accordingly, it may be advantageous to grow the first seeded culture and/or subsequent co-cultures to other confluences as to account for growth rates of previously seeded cultures with subsequently seeded cultures and/or the desired cellular composition of the final co-culture.

The composition of serum generated by a co-culture of cells may also be altered by cells becoming senescent. Cells are more productive when they are actively proliferating. Additionally, cells in the proliferative phase produce different molecular factors then senescent cells. Having altered and/or diminished production of molecular factors, a co-culture comprising senescent cells may also be unlikely to produce a serum having all the proteins and/or other molecular factors necessary for healing and/or promoting the health of injured and/or aging organs. Preserving intercellular signaling and/or maintaining cells in the proliferative phase in a co-culture of cells, accordingly, may provide a therapeutic serum suitable for promoting the health and/or healing of various organs. Therefore, it may be desirable to maintain cultures from which cells are to be harvested for co-culturing in a proliferative phase. Likewise, it may be desirable to maintain cells within seeded cultures in a proliferative phase.

Maintaining cells within a culture in a proliferative phase may be accomplished by preventing the culture form achieving one-hundred percent confluence. Accordingly, as to maintain the cells of the first seeded culture in a proliferative phase, the first seeded culture should be grown to a monolayer of less than one-hundred percent confluence, as to provide at least one cell free area on the surface. After the first culture has been established, a second culture may be seeded onto all or a portion of the cell free areas. The first and second culture may then be grown to less than one hundred percent confluence.

The cells of the second or other subsequent cultures seeded onto the surface having a monolayer of preceding cultures may be provided in suspension. The suspension may be acquired from one or more separately grown cultures. Such separate cultures may be grown on a surface and/or in suspension in the presence of a growth medium including growth factors and nutrients. The nutrients provided in the growth medium of the cultures from which cells to be seeded are harvested do not need to be lavish or exceed the minimal nutrients required for survival and growth of the culture. As such, a basal medium and/or minimal essential medium can provide sufficient nutrients. Accordingly, the growth medium provided to cultures from which cells are harvested may comprise growth factors combined with a basal medium and/or minimal essential medium. The growth medium provided to subsequent cultures may include a balancing agent to buffer the medium to a desired pH, such as, but not limited to, Earl's salts and/or HEPES.

Growth of subsequent cultures with the first culture after seeding may be facilitated and/or enhanced by maintaining the cells of subsequent cultures in a proliferative phase. Cells of subsequent cultures may be maintained in a proliferative phase by growing the cells on a second surface to less than one-hundred percent confluence prior to seeding onto the first surface of the co-culture. For instance, growing the cells of subsequent cultures on a second surface to approximately 80 to 90 percent confluence before seeding onto the surface of the co-culture may maintain the cells of the subsequent culture in a proliferative phase prior to seeding.

As to provide subsequent cultures a sufficient surface to become established, the first culture and/or preceding co-cultures are grown to monolayers of less than one-hundred percent confluence. For instance, the first culture and/or proceeding co-cultures may be grown to a monolayer of approximately eighty to ninety percent confluence, before seeding the second and/or subsequent cultures onto the at least one of the cell free areas of the first surface. Though previous cultures are grown to less than one-hundred percent confluence, it may be necessary to provide areas on the surface free of preceding cultures. Providing such surfaces within a monolayer of established cultures may be accomplished by growing preceding cultures to a monolayer of less than one-hundred percent confluence and then increasing the cell free surface area by creating voids in the monolayer of the first culture and/or preceding co-cultures by removing an appropriate amount of the monolayer. The amount removed will be dependent on the growth rate of the cells together and/or the final cellular composition of the co-culture desired. For example, if a co-culture comprising approximately equally amounts of two cell types is desired, and the second seeded cell type is sufficiently aggressively as to fill voids without allowing the first cells to significantly enter the voids, then approximately 50% of the monolayer of the first culture may be removed.

Voids may be created by removing portions of the monolayer of preceding cultures from the surface. For instance, voids may be created by scraping or otherwise mechanically detaching portions of the monolayer of the first culture and/or preceding co-cultures from the surface. It is also possible to remove portions of an established monolayer by first treating the monolayer with a detachment solution for a sufficient time to cause cells in the monolayer to begin to ball. Once the cells of the monolayer begin to ball, the detachment solution can be withdrawn and squirted back onto the monolayer to produce voids in the monolayer.

The serum collected from a co-culture of cells may be enhanced by maintaining the cells in a proliferative phase by growing the final co-culture to less than one-hundred percent confluence on the first surface after seeding the final culture to be added. Maintaining the cells in a proliferative phase prior to and/or during serum collection may influence the composition of the serum. The composition of the serum may be adjusted by allowing at least a portion of the cells to senesce. Accordingly, the composition and/or ratio of senesced versus proliferative cells within the co-culture may influence the composition and/or quality of the serum collected.

The quality of the serum may also be enhanced by stressing the cells within the co-culture. Cells within the co-culture may be stressed by selectively depriving the cells of at least one growth factor, nutrient and/or metabolic component. For example, cells within the co-culture may be stressed by depriving the cells of one or more growth factors while maintaining nutrient levels. Cells within the co-culture may by stressed after the co-culture has grown to approximately 80 to 95% confluence or at other times. Accordingly, production of a therapeutic serum may be induced in a co-culture by replacing the first and/or second growth medium with a collection medium lacking all or a portion of the growth factors of the final growth medium, after the final co-culture has been grown to less than one-hundred percent confluence. For instance, the second growth medium may be replaced with a collection medium lacking at least one of the growth factors of the second growth medium. The collection medium may comprise the nutrients of at least one of the first and second growth mediums. The co-culture may then be maintained for a period of time in the collection medium sufficient to allow the co-culture to produce from the collection medium a conditioned medium comprising the therapeutic serum. After which, at least a portion of the conditioned medium containing the therapeutic serum may be collected.

As to facilitate further production of the therapeutic serum, the withdrawn portion of the conditioned medium may be replaced with fresh collection medium. Production of the therapeutic serum may also be enhanced by allowing the co-culture to recover from the induced stress. Such a recovery phase may be provided by replacing the conditioned medium with a recovery medium containing the removed growth factors and culturing the co-culture in the recover medium for a recovery period of time. Preventing the co-culture from obtaining one-hundred percent confluence may improve and/or maintain the quality of the serum produced. The recovery medium may comprise the growth factors and/or nutrients of at least one of the first, second and other growth medium utilized in establishing the co-culture. Depending on the cells included within the co-culture, a recovery period of approximately 24 to 72 hours may be sufficient.

The collected therapeutic serum may be applied to directly an organ. For instance, the serum may be sprayed onto exposed organs, such as skin, or organs exposed during surgery and/or injury. The therapeutic serum may also be injected into and/or around the organ intended for treatment.

The serum may also be incorporated into a delivery medium. For instance, after the therapeutic serum has been collected, a delivery medium comprising a cosmetic preparation may be produced by adding the therapeutic serum to a cosmetically suitable base. Accordingly, a cosmetic preparation may comprise a serum prepared by any of the above detailed processes and a cosmetic base. The cosmetic base which may be used is not particularly limited and may comprise at least one of a hydrogel, such as polyethylene glycol, an oil, such as sunflower seed oil, sweet almond oil and/or coconut oil, and/or a fat, such as Shea Butter, or various combinations thereof. The cosmetic base may also include alcohols, polyols, emulsifiers, such as Ceteareth-20, carbomer and/or glycerol monostearate, preservatives, and/or moisturizers, such as hyaluronic acid. An Antioxidant, such as vitamin E, vitamin A and/or vitamin C may also be included in the composition. The cosmetic preparation may include phytochemicals, such as resveritol, quercetin and/or epigallocatechin gallate. If desired, a fragrance may also be added to the cosmetic preparation. The cosmetic preparation may contain other ingredients, such as pigments, flavoring agents, preservatives and/or sweeteners. The ingredients included within the cosmetic preparation are not particularly limited, as long as they collectively provide a cosmetically suitable preparation that is non-toxic when topically applied.

The delivery medium may comprise a physical structure such as a gauze, mesh, bandage and/or dressing. For instance, a serum derived from skin cells for treating wounds may be incorporated into a wound dressing, such as silicone mesh, dressing, bandage or gauze. The wound dressing should be sufficiently porous and/or have sufficient internal spaces as to hold and elude a therapeutically effective amount of the serum.

The physical structure may also comprise an implantable structure, such as a biocompatible mesh. The mesh may be placed over, adjacent and/or within the organ to be treated. For instance, a serum derived from a co-culture cells of liver cells may be placed in proximity to the liver. The implantable structure should be sufficiently porous and/or have sufficient internal spaces as to hold and elude a therapeutically effective amount of the serum. The implantable structure may be bioabsorbable as eliminate the need for subsequent surgeries to retrieve the structure. Additionally, absorption of the structure by the body may facilitate release of a therapeutic effective amount of the serum over time. Appropriate bioabsorbable structures may be fabricated from poly(hydroxyvalerate), poly(L-lactic acid), polcaprolactone, poly(lactide-co-glycolide), poly(hydroxybutyrate), poly(hydroxybutyrate-co-valerate), polydioxanone, polyorthoesters, polyanhydrides, poly(glycolic acid), poly(D.L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphaZenes and biomolecules such as fibrin, fibrinogen, cellulose, starch, collagen, hyaluronic acid, etc., and mixtures thereof.

The delivery medium may also comprise a graft in which the therapeutic serum is infused. For instance, the therapeutic serum may be provided within a skin graft and/or vascular graft. The graft may be supported by a matrix. Matrixes supporting the graft may be composed of any biocompatible material. In some instances, the matrix supporting the graft may comprise bioabsorable materials, such as poly(hydroxyvalerate), poly(L-lactic acid), polcaprolactone, poly(lactide-co-glycolide), poly(hydroxybutyrate), poly(hydroxybutyrate-co-valerate), polydioxanone, polyorthoesters, polyanhydrides, poly(glycolic acid), poly(D.L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphaZenes and biomolecules such as fibrin, fibrinogen, cellulose, starch, collagen, hyaluronic acid, etc., and mixtures thereof. In some instance, the graft may only comprise the matrix.

As to better match the individual to be treated, the co-culture of cells providing the therapeutic serum may be harvested from the patient to be treated and/or related individual.

DETAILED DESCRIPTION

A method for obtaining a therapeutic serum suitable for inclusion in now will be described more fully with reference to specific examples. The serum, however, may be obtained in different manners, and thus should not be construed as limited to the specific examples provided. Accordingly, the serum may be obtained by a different ordering and/or sequence of the various steps and/or procedures detailed in the provided examples. For example, two or more steps may be performed concurrently or with partial concurrence. Also, some steps that are performed as discrete steps in the following examples may be combined, and steps being performed as a combined step may be separated into discrete steps, the sequence of certain steps may be reversed or otherwise varied, and the nature or number of discrete steps may be altered or varied. Accordingly, the provided examples are not intended to exclude any of such means of obtaining a therapeutic serum suitable for use in a cosmetic preparation.

Likewise, different reagents, techniques, materials and/or equipment other than those specifically mentioned may be utilized to provide the therapeutic serum.

A therapeutic serum may be produced by stressing a co-culture including proliferative cells. The co-culture of cells may be obtained by first establishing a monolayer of a first cell culture on a surface. After a monolayer of a first culture is established, a second culture may then be seeded onto cell free areas within the monolayer and established. Additional cultures may then be seeded and established until a monolayer the having the desired cellular composition is obtained. The monolayer of the final co-culture is then stressed to obtain a serum by conditioning with a collection medium. The obtained serum may be incorporated into a suitable delivery medium.

For instance, a serum comprising Human Neonatal Fibroblast/Keratinocyte Conditioned Media may be obtained from a proliferative monolayer comprising a co-culture of keratinocytes and fibroblasts. The co-cultured monolayer may be established by first partially submerging a vial of frozen keratinocytes (obtained from LifeLine Cell Technologies) in a 37° C. water bath, without submerging the top of the vial. The vial is allowed to thaw in the water bath until a small piece of ice remains. The vial is then removed and sprayed with an ethanol solution. In a hood, keratinocytes are seeded from the vial at 2,500 to 5,000 cells per $cm^2$ onto a culture treated surface. The surface should be provided with an appropriate volume of a suitable growth medium, such as a medium including Basal DermaLife Media (LifeLine Cell Technologies) and growth factors comprising bovine pituitary extract, L-glutamine, hydrocortisone hemisuccinate, transforming growth factor, insulin, epinephrine and/or ApoTransferrin. The seeded surface is then placed in an incubator and grown at 37° C. in the presence of humidified air comprising 5% $CO_2$. As to remove any residue DMSO and/or other solvents that may be present in the cryogenic solution, the growth medium may be changed every 24 to 48 hours following initiation of the monoculture. After which time, the growth medium may be changed every 48 to 72 hours.

Other means of obtaining the initial keratinocytes may also be employed. For instance, keratinocytes may be isolated from neonatal foreskin retrieved from circumcision using the techniques detailed in U.S. application Ser. No. 14/597,796, filed Jan. 15, 2015, the teachings of which are hereby incorporated by reference in their entirety.

The keratinocytes are allowed to grow in the growth medium until 80-90% confluence is achieved. Voids are then created within the established monolayer by removing the growth medium and washing twice with an appropriate volume of a buffer solution, such as phosphate buffer solution without calcium or magnesium. After washing with buffer solution, a sufficient volume of an enzymatic cell detachment solution to promote detachment of the cells from the surface is added. The cell detachment solution may comprise proteolytic and/or collagenolytic enzymes. For instance, detachment of the cells may be promoted by adding 1 ml of HyQTase Solution, manufactured by HyClone Laboratories, Inc, per 25 $cm^2$ of growth area. The enzymatically treated monolayer may then be incubated at 37° C. until the keratinocytes start balling. The surface is then tilted to collect the enzyme solution with a pipette. The collected solution is sprayed at focused points onto the monolayer to create voids in about 50% of the monolayer. The enzyme solution and detached keratinocytes are then removed. The remaining monolayer is provided with a sufficient volume of the growth medium and returned to the incubator. For example, an amount of medium providing 10 ml of medium per 55 $cm^2$ of growth area may be sufficient.

Simultaneously, a monolayer of fibroblasts is cultured on a second surface by submerging a vial of frozen fibroblasts (obtained from LifeLine Cell Technologies) in a 37° C. water bath, without submerging the top of the vial. The vial is allowed to thaw in the water bath until a small piece of ice remains. The vial is then removed and sprayed with an ethanol solution. In a hood, fibroblasts are seeded from the vial at 2,500 to 5,000 cells per $cm^2$ on to a culture treated surface. The surface should be provided with an appropriate volume of a suitable growth medium, such as a medium including Basal DermaLife Media (LifeLine Cell Technologies) and growth factors comprising L-glutamine, hydrocortisone hemisuccinate, lineolic acid, licithin, human serum albumin, basic fibroblasts growth factor, epidermal growth factor, transforming growth factor, insulin and/or vitamin C. The seeded surface is then placed in an incubator and grown at 37° C. in the presence of humidified air comprising 5% $CO_2$. As to remove any residue DMSO and/or other solvents that may be present in the cryogenic solution, the growth medium may be changed every 24 to 48 hours following initiation of the monoculture. After which time, the growth medium may be changed every 48 to 72 hours.

Other means of obtaining the initial fibroblasts may also be employed. For instance, fibroblasts may be isolated from neonatal foreskin retrieved from circumcision using the techniques detailed in co-pending U.S. application Ser. No. 14/597,796.

When the fibroblast monolayer reaches approximately 80 to 90% confluence, the surface is transferred to a hood and the growth medium removed. The fibroblasts monolayer is then washed with a buffer solution, such as phosphate buffer solution without calcium or magnesium. A sufficient volume of a cell detachment solution to promote detachment of the fibroblasts from the second surface is then added. For instance, detachment of the fibroblasts may be promoted by adding 1 ml of Accutase Cell Detachment Solution, manufactured by Innovative Cell Technologies, Inc, per 25 $cm^2$ of growth area. The fibroblast cells are then incubated in the cell detachment solution at 37° C. until all the cells have detached. A homogenous suspension of cells is then obtained by mixing and the fibroblasts suspension is seeded onto cell free areas within the keratinocyte monolayer. The seeded culture is then returned to the incubator. The co-culture is then grown in the keratinocyte growth medium until 80 to 95% confluence is achieved.

A monolayer of co-cultured cells may also be achieved by culturing keratinocytes in the keratinocyte growth medium until approximately 50% confluence is achieved. Cell free areas on the surface may then be seeded with the cultured fibroblasts suspension. For example, a co-culture in a T175 $cm^2$ flask would be overlayed with 1.5 ml of fibroblast suspension generated from a confluent T75 $cm^2$ flask of fibroblasts dissociated using 3 ml of Accutase. The co-culture may then be grown in the incubator until approximately 80 to 95% confluence is achieved.

The co-culture of cells may be stressed to provide a therapeutic serum suitable for use in a cosmetic preparation. Stressing the co-culture may be achieved by selectively removing nutrients, growth factors and/or other favorable conditions. The stress need not be severe. Accordingly, sufficient stress may be induced by removing all or a portion of the growth factors while maintaining nutrient levels. Growth factors may be removed by extracting the keratinocyte growth medium from the surface and rinsing the co-culture monolayer twice with a sufficient volume of a buffer solution, such as phosphate buffer solution lacking calcium and magnesium. As to ensure all growth factors are removed, the co-culture may be incubated for a period of time in a collection medium that is added to the surface and then discarded prior to serum collection. For instance, growth factors may be removed prior to serum collection by adding approximately 5.0 ml of a collection medium per 55 $cm^2$ of growth area and incubating for approximately six hours.

The collection medium may comprise a minimum essential medium with Earl's salt and have the nutrients of the keratinocyte growth medium.

After removal of the growth factors, a sufficient volume of fresh collection medium is added, and the surface returned to the incubator for a sufficient period of time to produce a conditioned medium form the collection medium. For example, incubating the co-culture in approximately 10.0 ml of fresh collection medium per 55 $cm^2$ of growth area for approximately 48 hours may be sufficient to produce a conditioned medium from the collection medium. After incubating for a sufficient period of time, approximately 50% of the collection medium is removed and replaced with an approximately equal amount of fresh collection medium. The co-culture is then incubated for approximately 48 hours to produce more conditioned medium. After which time, all of the conditioned medium is removed.

The co-culture is then allowed to recover by removing the stress and incubating for a period of time. For instance, incubating in the presence of approximately 10.0 ml per 55 $cm^2$ of growth area of the keratinocyte growth medium for approximately 24 to 72 hours may provide sufficient recovery. During recovery, the co-culture may be refreshed by seeding fresh cells of one or more of the cultures onto the monolayer.

After recovering, serum collection is repeated.

The process of the serum collection and recovery may be repeated until the co-cultures no longer produce serum of the desired quality. For instance, three passes may be utilized. The quality of serum may begin to degrade when one or more of the cultures used to initially establish the co-culture reach 80% of their life expectancy as defined by the maximum number of population doublings.

The conditioned medium collected may be filtered using a suitable filter, such as a 0.45 μm Millipore filter. The serum collected from filtering the conditioned medium may be tested for sterility, virology and/or stability factors. Depending on the intended use of the serum, such testing may not be necessary.

The therapeutic serum collected may be incorporated into a suitable delivery medium. For instance, a cosmetic base incorporating the therapeutic serum may provide therapeutic cosmetic preparation useful as a recovery cream, moisturizer, neck cream, eye cream and/or facial cream. After combining the therapeutic serum to the base, antioxidants, and/or fragrances may be added to the cosmetic preparation. The cosmetic preparation may comprise approximately 58 to 77 percent by mass of base, approximately 2 to 5 percent by mass of a moisturizer, approximately 9 to 33 percent by mass of the serum, 3 to 14 percent by mass of antioxidants, and approximately 0 to 0.01 percent by mass of fragrance. Other amounts and/or ingredients collectively providing a cosmetically suitable preparation may be utilized in combination with the serum.

In an exemplary embodiment, a facial cream cosmetic preparation may be prepared by adding 2.35 mass percent super low molecular weight hyaluronic acid added to 58.92 mass percent base. The base and hyaluronic acid combination may then be slowly mixed until homogenous. After which, 29.45 mass percent serum may be added to the base and hyaluronic acid mixture and slowly mixed until a homogenous mixture is obtained. Then 5.89 mass percent vitamin C may be slowly mixed in to provide a homogenous mixture. After providing a homogenous mixture including vitamin C, 2.94 mass percent vitamin E may be slowly mixed in to provide a homogenous mixture. Then 0.44 mass percent vitamin A may be mixed in to provide a final homogenous vitamin-base-moisturizer-serum composition. To this composition, 0.01 mass percent fragrance may be mixed in to provide a final homogenous cosmetic preparation.

In an exemplary embodiment, an eye cream cosmetic preparation may be prepared by combining 61.83 mass percent base with 30.90 mass percent serum and slowly mixing until a homogenous mixture of base and serum is obtained. To this mixture, 3.707 mass percent super low molecular weight hyaluronic acid may be slowly mixed in to provide a homogenous mixture. Then, 3.09 mass percent vitamin E may be slowly mixed in to provide another homogenous mixture. To this mixture, 0.463 mass percent vitamin A may be slowly mixed in to provide a homogenous vitamin-base-moisturizer-serum composition. To this composition, 0.01 mass percent fragrance may be slowly mixed in to provide a final homogenous cosmetic preparation.

In an exemplary embodiment, a neck cream cosmetic preparation may be prepared by combining 67.243 mass percent base with 16.810 mass percent serum, and mixing slowly to provide a homogenous mixture of base and serum. To this mixture 4.203 mass percent super low molecular weight hyaluronic acid may be slowly mixed in to provide a homogenous mixture. Then, 7.985 mass percent vitamin C may be slowly mixed in to provide a homogenous mixture. To this homogenous mixture, 3.329 mass percent vitamin E may be slowly mixed in to provide another homogenous mixture. After which, 0.42 mass percent vitamin A may be slowly mixed in to provide a homogenous vitamin-base-moisturizer-serum composition. To this composition, 0.01 mass percent fragrance may be mixed in to provide a final homogenous cosmetic preparation.

In an exemplary embodiment, a moisturizer cream cosmetic preparation may be prepared by combining 76.100 mass percent base with 9.605 mass percent serum and mixing slowly until a homogenous base-serum mixture is obtained. To this mixture, 3.42 mass percent super low molecular weight hyaluronic acid may be slowly mixed to provide another homogenous mixture. To this mixture, 6.60 mass percent vitamin C may be slowly mixed in to provide a homogenous mixture. After which, 3.805 mass percent vitamin E may be slowly mixed in to provide a homogenous mixture. Then, 0.46 mass percent vitamin A may be slowly mixed in to provide a homogenous vitamin-base-serum-moisturizer composition. To this composition, 0.01 mass percent fragrance may be mixed in to provide a cosmetic preparation.

In an exemplary embodiment, a recovery cream cosmetic preparation may be prepared by combining 66.67 mass percent base with 33.33 mass percent serum and mixing slowly until homogenous.

While the present invention has been described herein with respect to the exemplary embodiments, it will become apparent to one of ordinary skill in the art that many modifications, improvements and sub-combinations of the various embodiments, adaptations and variations can be made to the invention without departing from the spirit and scope thereof. Accordingly, the presented embodiment should not be construed as limiting the scope of this disclosure or the accompanying claims.

Furthermore, it should be appreciated that "first" and "second" as used in claims is merely to reference that one (first) precedes another (second) and/or to distinguish similar components from one another. It should also be appreciated that though examples presented above may have included only two cultures, this was solely for purposes of illustration and in no way intended to limit the scope of this disclosure or the claims. As such, a "first culture" may be a first, second, third, etc. culture. Likewise, the "second culture" may be any culture added subsequent to the "first culture". Accordingly, if the "first culture" is the third culture added, then the "second culture" may be a fourth, fifth, sixth, etc. culture.

What is claimed:

1. A method of producing a serum, comprising the steps of:
    (a) seeding a first surface with a first culture of cells;
    (b) growing the first culture to a monolayer of less than 100% confluence in the presence of a first growth medium, to provide at least one cell free area on the first surface, the first growth medium comprising nutrients and at least one growth factor, wherein the first growth medium promotes proliferation of the first culture;
    (c) seeding a second culture onto the at least one cell free area of the first surface, the second culture comprising cells different from those of the first culture;
    (d) growing the first and second culture to less than 100% confluence in the presence the second growth medium, the second growth medium comprising of nutrients and at least one growth factor, wherein the second growth medium promotes proliferation of the second culture;
    (e) after growing the first and second cultures to less than 100% confluence, replacing the second growth medium with a collection medium, the collection medium lacking at least one of the growth factors of the second growth medium;
    (f) maintaining the first and second cultures for a period of time in the presence of the collection medium to produce a conditioned medium; and
    (g) collecting at least a portion of the conditioned medium after the period of time, said conditioned medium comprising a therapeutic serum.

2. The method of claim 1, wherein the first culture is grown to a monolayer of approximately 80 to 90% confluence, before seeding the second culture onto the at least one cell free area of the first surface.

3. The method of claim 1, further comprising:
    before seeding the second culture onto the first surface, increasing the cell free surface area of on the first surface by creating voids in the monolayer of the first culture.

4. The method of claim 3, wherein creating voids in the monolayer of the first culture comprises mechanically detaching a portion of the monolayer of the first culture.

5. The method of claim 3, wherein creating voids in the monolayer of the first culture comprises:
    treating the monolayer of the first culture with a detachment solution;
    after cells within the monolayer of the first culture begin to ball, removing the detachment solution; and
    squirting the monolayer of the first culture with the detachment solution.

6. The method of claim 5, wherein the detachment solution comprises a proteolytic enzyme and a collagenolytic enzyme.

7. The method of claim 1, wherein the nutrients of the first growth medium are provided by a basal medium.

8. The method of claim 1, wherein the growth factors of the first growth medium comprise at least one of bovine pituitary extract, L-glutamine, hydrocortisone hemisuccinate, transforming growth factor, insulin, epinephrine, and ApoTransferrin.

9. The method of claim 1, wherein the second growth medium comprises the nutrients and at least one growth factor of the first medium.

10. The method of claim 1, wherein the nutrients of the second growth medium are provided by a basal medium.

11. The method of claim 1, wherein the growth factors of the second growth medium comprise at least one of L-glutamine, hydrocortisone hemisuccinate, lineolic acid, lecithin, human serum albumin, basic fibroblasts growth factor, epidermal growth factor, transforming growth factor, insulin, and vitamin C.

12. The method of claim 1, further comprising growing the second culture on a second surface to less than 100% confluence before seeding onto the first surface.

13. The method of claim 1, wherein the collection medium comprises the nutrients of at least one of the first growth medium and the second growth medium.

14. The method of claim 1, further comprising:
after collecting at least a portion of the conditioned medium, replacing the conditioned medium with a recovery medium; and
culturing the first culture and second culture in the recovery medium for a recovery period of time.

15. The method of claim 14, wherein the recovery medium comprises:
the growth factors of at least one of the first growth medium and the second growth medium; and
the nutrients of at least one of the first growth medium and the second growth medium.

16. The method of claim 1, wherein the second culture comprises cells having a faster growth rate than those of the first culture.

* * * * *